(12) United States Patent
Dupau et al.

(10) Patent No.: US 8,236,749 B2
(45) Date of Patent: Aug. 7, 2012

(54) ACETALS AS PERFUMING INGREDIENTS

(75) Inventors: Philippe Dupau, Bellegarde (FR); Murielle Haldimann Sanchez, Valleiry (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/257,371

(22) PCT Filed: Apr. 14, 2010

(86) PCT No.: PCT/IB2010/051608
§ 371 (c)(1),
(2), (4) Date: Sep. 19, 2011

(87) PCT Pub. No.: WO2010/122451
PCT Pub. Date: Oct. 28, 2010

(65) Prior Publication Data
US 2012/0010114 A1    Jan. 12, 2012

(30) Foreign Application Priority Data
Apr. 21, 2009 (EP) .................... 09158371

(51) Int. Cl.
*A61K 8/00* (2006.01)
(52) U.S. Cl. .................. 512/23; 510/106; 568/591
(58) Field of Classification Search ........... 510/106; 512/23; 568/591
See application file for complete search history.

(56) References Cited

U.S. PATENT DOCUMENTS

| | | | |
|---|---|---|---|
| 4,594,456 A | 6/1986 | Schaefer-Luederssen et al. | 568/447 |
| 5,175,143 A | 12/1992 | Newman et al. | 512/12 |
| 6,177,400 B1 | 1/2001 | Mimoun et al. | 512/24 |

FOREIGN PATENT DOCUMENTS

| | | | |
|---|---|---|---|
| EP | 114612 | * | 8/1984 |
| EP | 0 955 290 B1 | | 11/1999 |
| FR | 2 338 241 A1 | | 8/1977 |
| GB | 1 541 972 A | | 3/1979 |

OTHER PUBLICATIONS

M.W. Tjepkema et al., Canadian Journal of Chemistry 1997, vol. 75, issue 9, pp. 1215-1224 (abstract).*
T. Mukaiyama, Organic Reactions 1982, vol. 28, no pp. given (abstract).*
International Search Report and Written Opinion of the International Searching Authority, application No. PCT/IB2010/051608 mailed Jul. 29, 2010.

* cited by examiner

*Primary Examiner* — John Hardee
(74) *Attorney, Agent, or Firm* — Winston & Strawn LLP

(57) ABSTRACT

Acetal derivatives of 2,2,3,6-tetramethyl-1-cyclohexane/ene-carbaldehyde of formula (I):

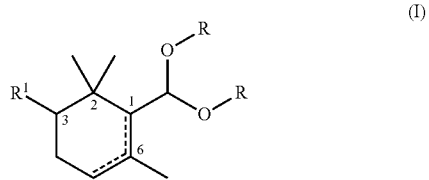

for use in the perfumery industry as well as the resulting compositions or articles containing one or more of these compounds. In formula (I), one dotted line indicates the presence of a carbon-carbon single or double bond and the other dotted line indicates the presence of a carbon-carbon single bond, $R^1$ represents a hydrogen atom or a methyl or ethyl group; and each R, taken alone, simultaneously or independently, represents a $C_{1-3}$ alkyl or alkenyl group, or the R groups, taken together, represent a $C_{2-6}$ hydrocarbon group optionally including an oxygen atom.

15 Claims, No Drawings

ACETALS AS PERFUMING INGREDIENTS

This application is a 371 filing of International Patent Application PCT/IB2010/051608, filed Apr. 14, 2010.

TECHNICAL FIELD

The present invention relates to the field of perfumery. More particularly, it concerns some acetal derivatives of 2,2,3,6-tetramethyl-1-cyclohexane/ene-carbaldehyde. The present invention concerns the use of said compounds in the perfumery industry as well as the compositions or articles containing said compounds.

PRIOR ART

To the best of our knowledge, the compounds of formula (I), described herein below, and wherein $R^1$ is a methyl group, are all new compounds. However, some of the compounds of formula (I) wherein $R^1$ is a hydrogen atom are described in the literature (e.g. see U.S. Pat. No. 4,594,456 or FR 2338241) but are described as chemical intermediates or starting materials in chemical processes.

None of the documents reporting an invention's compounds suggests that the present compounds could have their specific odor (as reported further below) or even an odor at all.

DESCRIPTION OF THE INVENTION

We have now surprisingly discovered that a compound of formula

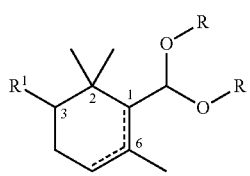

(I)

wherein one dotted line indicates the presence of a carbon-carbon single or double bond and the other dotted line indicates the presence of a carbon-carbon single bond;
$R^1$ represents a hydrogen atom or a methyl or ethyl group; and
each R, taken alone, simultaneously or independently, represents a $C_{1-3}$ alkyl or alkenyl group; or said R groups, taken together, represent a $C_{2-6}$ hydrocarbon group optionally comprising an oxygen atom;
can be used as perfuming ingredient, for instance to impart odor notes of the woody and/or earthy, camphoraceous type.

According to a particular embodiment of the invention, said compound (I) is a compound of formula

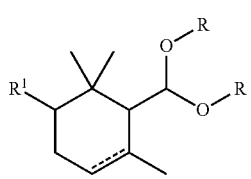

(II)

wherein the dotted line indicates the presence of a carbon-carbon single or double bond;
$R^1$ represents a hydrogen atom or a methyl group; and
each R, taken alone, simultaneously or independently, represents a $C_{1-2}$ alkyl group; or
said R groups, taken together, represent a $C_{2-5}$ hydrocarbon group.

According to any one of the above embodiments, $R^1$ represents a methyl group. According to any one of the above embodiments, the dotted line represents a carbon-carbon single bond.

According to any one of the above embodiments, said R groups are taken together and represent a $C_{2-4}$ hydrocarbon group, such as $CH_2CH_2$, $CH_2CH_2CH_2$, $CHMeCH_2$, $CHMeCHMe$, $CH_2CHMeCH_2$, $CH_2CHEt$ or $CH_2CMe_2CH_2$.

According to any one of the above embodiments, said invention's compound can be in the form of any one of its stereoisomers, or enantiomers, or in the form of a mixture thereof, e.g can be a racemic or optically active compound.

According to a particular embodiment, and in particular when all dotted lines represent a single bond, said compound is in the form of a mixture of stereoisomers comprising more than 50% (w/w) of the stereoisomer wherein the substituents at positions 1 and 6 of the cyclohexane ring are in a trans relative configuration, and preferably when $R^1$ is a methyl group the substituents at positions 3 and 6 of the cyclohexane ring are in a trans relative configuration.

For the sake of clarity, by the expression "one dotted line indicates the presence of a carbon-carbon single or double bond and the other dotted line indicates the presence of a carbon-carbon single bond", or the similar, it is meant the normal meaning understood by a person skilled in the art, i.e. that the whole bonding (solid and dotted line) between the carbon atoms connected by said dotted line can be a carbon-carbon single or a double bond.

The invention's compounds wherein $R^1$ represents a methyl group are new compounds and therefore are another object on the invention.

As typical examples of the invention's compounds, one may cite those described in Table (I) herein below, together with their odors:

TABLE 1

Structure and odor characteristics of the invention's compounds

| Structure of compound (I) | Odor |
|---|---|
| Trans-2-(2,5,6,6-tetramethyl-2-cyclohexen-1-yl)-1,3-dioxolane | Nice odor of the woody, floral-orris type, together with a balsamic connotation |
| Mixture of cis-2-(2,5,6,6-tetramethyl-2-cyclohexan-1-yl)-1,3-dioxolane and 2-(2,5,6,6-tetramethyl-1-cyclohexen-1-yl)-1,3-dioxolane | Compared to the above compound, the odor of this mixture is more woody, ambery, as well as less floral and orris. Also a balsamic, liquorice bottom note |

TABLE 1-continued

Structure and odor characteristics of the invention's compounds

| Structure of compound (I) | Odor |
|---|---|
| 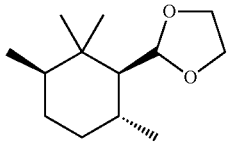<br>2-(2,2,c-3,t-6-Tetramethyl-r-1-cyclohexyl)-1,3-dioxolane | Very nice woody compound, with a cedar sawdust connotation as well as a slight moss aspect |
| 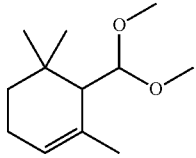<br>6-(Dimethoxymethyl)-1,5,5-trimethyl-1-cyclohexane | Generally evoking the odor of Bromarose (1,3-dibromo-2-methoxy-4-methyl-5-nitrobenzene). Learther, saffron, slightly damascony, with a thujonic aspect of the rose tea |
| 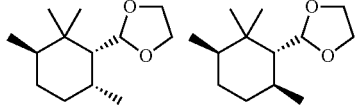<br>Mixture of 2-[(1RS,3RS,6RS)-2,2,3,6-tetramethylcyclohexyl]-1,3-dioxolane and 2-[(1RS,3RS,6RS)-2,2,3,6-tetramethylcyclohexyl]-1,3-dioxolane | Woody, camphoreceous odor |
| 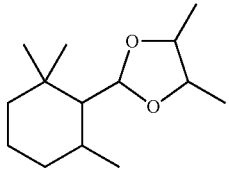<br>4,5-Dimethyl-2-(2,2,6-trimethyl-1-cyclohexyl)-1,3-dioxolane | Pleasant, earthy and camphoreceous, fresh-minty |
| 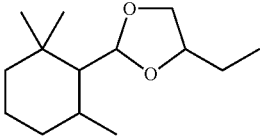<br>4-Ethyl-2-(2,2,6-trimethyl-1-cyclohexyl)-1,3-dioxolane | Powdery, camphoraceous, earthy |
| 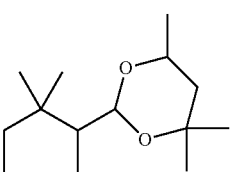<br>4,4,6-Trimethyl-2-(2,2,6-trimethyl-1-cyclohexyl)-1,3-dioxane | Pleasant, earthy and camphoreceous, green and hyacinth notes |

According to a particular embodiment the compounds trans-2-(2,5,6,6-tetramethyl-2-cyclohexen-1-yl)-1,3-dioxolane, 2-[(1RS,3RS,6RS)-2,2,3,6-tetramethylcyclohexyl]-1,3-dioxolane, 2-[(1RS,3RS,6SR)-2,2,3,6-tetramethylcyclohexyl]-1,3-dioxolane or 2-(2,2,c-3,t-6-Tetramethyl-r-1-cyclohexyl)-1,3-dioxolane are particularly appreciated.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)", it has to be understood here also the use of any compositions containing compound (I) and which can be advantageously employed in perfumery industry as active ingredients.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono-, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a fine or functional perfumery base;
is also an object of the present invention.

For the sake of clarity, it has to be mentioned that, by "fine or functional perfumery base" we mean here a consumer product which is compatible with perfuming ingredients and is expected to deliver a pleasant odor to the surface to which it is applied (e.g. skin, hair, textile, or home surface). In other words, a consumer product for the purpose of perfuming according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the fine or functional perfumery base do not warrant a more detailed description here, which in any case would not be exhaustive, the skilled person being able to select them on the basis of his general knowledge and according to the nature and the desired effect of said product.

Non-limiting examples of suitable fine or functional perfumery base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 20% by weight, or even more, of the compounds of the invention based on the weight of the composition into which they are incorporated. Concentrations lower than these, such as in the order of 0.001% to 10% by weight, can be used when these compounds are incorporated into perfumed articles, percentage being relative to the weight of the article.

The invention's compounds can be prepared from the stereoisomers, or mixture thereof, of the known aldehyde

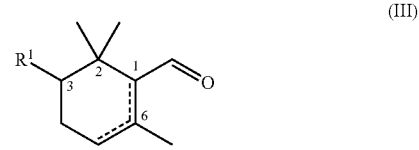

(III)

wherein the dotted lines and $R^1$ have the same meaning as in formula (I);
by reacting said starting material with a suitable alcohol or diol. A typical example is provided in the Examples herein below.

EXAMPLES

The invention will now be described in further detail by way of the following examples, wherein the abbreviations have the usual meaning in the art, the temperatures are indicated in degrees centigrade (° C.); the NMR spectral data were recorded in CDCl₃ (if not stated otherwise) with a 360 or 400 MHz machine for ¹H and ¹³C, the chemical shifts δ are indicated in ppm with respect to TMS as standard, the coupling constants J are expressed in Hz.

Example 1 a) Preparation of trans-2-(2,5,6,6-tetramethyl-2-cyclohexen-1-yl)-1,3-dioxolane and of a cis-2-(2,5,6,6-tetramethyl-2-cyclohexen-1-yl)-1,3-dioxolane and 2-(2,5,6,6-tetramethyl-1-cyclohexen-1-yl)-1,3-dioxolane mixture 2,5,6,6-Tetramethyl-cyclohexene carbaldehyde (64/7/29 trans 2-ene/cis 2-ene/1-ene isomers mixture) (1660 g, 10 mol., 1 eq.), ethylene glycol (1240 g, 20 mol., 2 eq.), cyclohexane (1660 g) and p-toluene sulfonic acid monohydrate (7.6 g, 0.04 mol., 0.004 eq.) were loaded altogether in a 10 liter schmizo type reactor equipped with a heating circulator, temperature probe, mechanical stirring device and a Dean-stark apparatus. The biphasic mixture was heated to reflux under vigorous stirring with azeotropic water removal from reaction mixture. After 8 hours reflux the reaction was then cooled down to room temperature. After decantation of the bottom phase containing excess ethylene glycol and p-toluene sulfonic acid the upper phase was concentrated under vacuum in order to remove cyclohexane and crude 2-(2,5,6,6-tetramethyl-cyclohexenyl)-1,3-dioxolane was obtained in 80% GC purity as a 80/7/13 trans 2-enyl/cis 2-en/1-enyl isomers mixture. Flash distillation afforded 1940 g of 2-(2,5,6,6-tetramethyl-cyclohexenyl)-1,3-dioxolane along with 60 g of residual heavy by-products formed during the reaction. Further purification was done using a 3 liter 3-necked flask equipped with a temperature probe, magnetical stirring device and a packed distillation column (3M Sulzer-type equivalent) distilling the mixture from 90 to 110° C. under 0.5 mbar vacuum using variable reflux rate. This last distillation provided:
 a first main fraction recovered is the remaining starting material;
 a second main fraction (1200 g) of trans 2-(2,5,6,6-tetramethyl-cyclohex-2-enyl)-1,3-dioxolane were obtained in 98.5% GC purity (57% molar yield); and
 a third main fraction consist of 280 g of a 1/1 cis 2-(2,5,6,6-tetramethyl-cyclohex-2-enyl)-[1,3]dioxolane and 2-(2,5,6,6-tetramethyl-cyclohex-1-enyl)-[1,3]dioxolane mixture in an overall 98% GC purity (13% molar yield).

trans-2-(2,5,6,6-tetramethyl-2-cyclohexen-1-yl)-1,3-dioxolane

¹H NMR: 5.49-5.45 (broad s, 1H, CH), 4.98 (d, J=2.7 Hz, 1H, CH), 4.02-3.95 (m, 1H, CH₂), 3.93-3.87 (m, 1H; CH₂), 3.84-3.72 (m, 2H, 2 CH₂), 2.07 (dm, J=18.1, 1H, CH₂), 1.95 (broad s, 1H, CH), 1.88-1.80 (m, 1H, CH), 1.77 (broad s, 3H, CH₃), 1.64-1.54 (m, 1H, CH₂), 1.00 (s, 3H, CH₃), 0.81 (d, J=6.8, 3H, CH₃), 0.78 (s, 3H, CH₃).
¹³C NMR: 132.00 (s), 123.51 (d), 104.98 (d), 65.08 (t), 63.70 (t), 54.15 (d), 34.15 (s), 32.66 (t), 32.07 (d), 25.98 (q), 25.38 (q), 21.35 (q), 15.36 (q).

cis-2-(2,5,6,6-tetramethyl-2-cyclohexen-1-yl)-1,3-dioxolane and 2-(2,5,6,6-tetramethyl-1-cyclohexen-1-yl)-1,3-dioxolane mixture ¹H NMR: 5.54-5.49 (m, 1H, CH), 5.32 (s, 1H, CH), 5.03 (broad s, 1H, CH), 4.14-4.04 (m, 3H, CH₂), 3.98-3.84 (m, 4H, CH₂), 3.82-3.76 (m, 1H, CH₂), 2.34 (broad s, 1H, CH) 2.12-2.01 (m, 1H, CH₂), 1.95 (dt, J=19.0 and 4.0, 1H, CH₂), 1.89-1.78 (m, 2H), 1.77 (s, 3H, CH₃), 1.75-41.71 (broad s, 3H, CH₃) 1.55-1.33 (m, 4H), 1.09 (s, 3H, CH₃), 1.02 (s, 3H, CH₃), 0.93 (s, 3H, CH₃), 0.89 (d, J=6.4 Hz, 3H, CH₃), 0.86 (d, J=6.8, 3H, CH₃), 0.77 (s, 3H, CH₃).
¹³C NMR: 137.19 (s), 132.62 (s), 132.40 (s), 124.66 (d), 104.31 (d), 102.51 (d), 65.37 (t), 64.68 (t), 64.29 (t), 62.98 (t), 51.78 (d), 39.52 (d), 38.66 (d), 36.80 (s), 34.42 (s), 33.15 (t), 31.50 (t), 27.09 (q), 26.94 (t), 26.43 (q), 23.07 (q), 21.55 (q), 20.08 (q), 16.27 (q), 15.28 (q), 15.19 (q).

b) Preparation of 2-(2,2,c-3,t-6-tetramethyl-r-1-cyclohexyl)-1,3-dioxolane

A mixture of 2,2,c-3,t-6-tetramethyl-cyclohexane carbaldehyde (5.0 g, 30 mmol), ethylene glycol (7.3 ml, 45 mmol), p-toluene sulfonic acid (0.3 g) in toluene (50 ml) was heated at reflux for 2.5 hours with a Dean-Stark apparatus. After concentration under vacuum, the residue was bulb-to-bulb distilled to afford pure acetal in 55% yield.
Bp: 73° C./0.95 mbar.
¹H NMR: 5.00 (s, 1H); 4.04 (m, 1H); 3.89 (m, 2H); 3.76 (m, 1H); 1.73 (m, 1H); 1.61 (m, 1H); 1.36 (m, 1H); 1.25 (m, 3H); 1.04 (m, 1H); 1.01 (s, 3H); 0.91 (d, J=7, 3H); 0.84 (d, J=7, 3H); 0.76 (s, 3H).

c) Preparation of 6-(dimethoxymethyl)-1,5,5-trimethyl-1-cyclohexene

This compound was obtained through transacetalisation reaction. To a stirred solution of 2-(2,6,6-trimethyl-2-cyclohexen-1-yl)-[1,3]-dioxolane (24.48 g, purity 89%, 111 mmol) in MeOH (125 ml) and 2,2-dimethoxypropane (125 ml) was added Filtrol G24 (4.90 g) and the mixture was stirred at room temperature during 24 h. The solids were filtered off, the filtrate was diluted with ether, washed (twice) with saturated aqueous NaHCO₃, dried (K₂CO₃) and concentrated to a yellow liquid (23.5 g). Distillation (10 cm-Widmer column) under vacuum (bp. 36-39° C./0.3 mbar) afforded 87% pure dimethyl acetal (17.97 g; 71%). The product was stirred over K₂CO₃ (1.57 g, 11.4 mmol) while bubbling air through the liquid at room temperature during 2.5 days. The mixture was diluted with ether, washed with saturated aqueous NaHCO₃, dried (K₂CO₃) and concentrated to a yellow liquid (17.14 g). Distillation (10 cm-Vigreux column) under vacuum gave 93% pure dimethylacetal (14.85 g; 63%),
Bp: 94-97° C./12 mbar.
¹H NMR: 0.90 (s, 3H), 0.96 (s, 3H), 1.10-1.18 (m, 1H), 1.58-1.67 (m, 1H), 1.81 (d, J=2, 3H). 1.85 (br. s, 1H), 1.89-2.08 (m, 2H), 3.38 (s, 3H), 3.41 (s, 3H), 4.29 (d, J=4, 1H), 5.50 (br. S, 1H).
¹³C NMR: 23.0 (t), 25.1 (q), 27.5 (q), 28.1 (q), 31.4 (s), 32.2 (t), 51.9 (d), 55.2 (q), 56.6 (q), 108.5 (d), 123.2 (d), 132.2 (s).

d) Preparation of a 2-[(1RS,3RS,6RS)-2,2,3,6-tetramethylcyclohexyl]-1,3-dioxolane and 2-[(1RS,3RS,6SR)-2,2,3,6-tetramethylcyclohexyl]-1,3-dioxolane mixture 2-(2,t-5,6,6-Tetramethyl-cyclohex-2-enyl)-[1,3]-dioxolane (630 g, 3 mol, 1 eq.) and 5 wt. % ruthenium on alumina (0.38 g ruthenium, 3.75 mmol., 0.00125 eq.) were loaded altogether in a 1 l autoclave. The sealed autoclave was purged under stirring with nitrogen (3 times 1 bar) and then hydrogen (3 times 1 bar). The autoclave was then pressurized to 40 bars hydrogen and then progressively heated to 120° C. under efficient mechanical stirring. After complete conversion was reached (6-8 hours in general), the autoclave was cooled down to room temperature, depressurized, purged with nitrogen and then opened. After heterogeneous catalyst filtration, desired product was obtained as a 3/1 to 4/1 2-(2,2,t-3,c-6-tetramethyl-cyclohexyl)-[1,3]-dioxolane/2-(2,2,t-3,t-6-tetramethyl-cyclohexyl)-[1,3]-dioxolane mixture in quantitative yield (635 g).

$^1$H NMR: 5.03 (d, J=2.1, 1H major, CH), 4.92 (s, 1H minor, CH), 3.62-3.54 (m, 1H minor), 3.54-3.45 (m, 2H major+1H minor), 3.38-3.31 (m, 1H minor), 3.30-3.22 (m, 2H major+1H minor), 2.10-1.93 (m, 2H major+1H minor), 1.89-1.70 (m, 2H major+2H minor), 1.56 (dq, J=13.3 and 4.2, 1H major), 1.46 (dq, J=13.3 and 4.6, 1H major), 1.42-1.18 (m, 1H major+4H minor), 1.18-1.10 (m, 6H major+6H minor), 0.97 (s, 3H minor, CH$_3$), 0.89 (s, 3H major, CH$_3$), 0.86 (d, J=7.1, 3H minor, CH$_3$), 0.84 (d, J=6.9, 3H major, CH$_3$).

$^{13}$C NMR: 105.70 (d), 105.05 (d), 65.11 (t), 63.89 (2 t), 62.98 (t), 51.85 (d), 48.49 (d), 41.21 (d), 36.63 (s), 36.14 (d), 35.18 (s), 31.67 (t), 31.09 (t), 30.76 (d), 29.17 (t), 28.83 (q$_3$), 28.76 (d), 28.19 (q), 24.91 (q), 23.27 (q), 22.51 (q), 20.92 (q), 16.35 (q), 15.15 (q).

General acetalysation procedure of
2,2,6-trimethyl-cyclohexane carbaldehyde 2,2,6-trimethyl-cyclohexane carbaldehyde (15.4 g, 0.1 mol, 1 eq.), 1, 2 or 1,3-diol (0.15 mol, 1.5 eq.), p-ptoluene sulfonic acid monohydrate (0.1 g, 0.5 mmol, 0.005 eq.) and heptane (100 ml) were loaded altogether in a 250 ml flask equipped with a Dean-Stark apparatus and the mixture was refluxed for 7 hours. It was then cooled down, washed with water and concentrated under vacuum. The obtained crude product was then purified by distillation.

e) Preparation of 4,5-dimethyl-2-(2,2,6-trimethyl-1-cyclohexyl)-1,3-dioxolane

According to the above general procedure, using the corresponding diol, the title compound was obtained in 89% yield.

$^1$H NMR (360.1 MHz): 5.27 (broad s), 5.15 (s), 5.14 (s), 4.90 (broad s), 4.37-4.00 (m), 3.66-3.51 (m), 1.85-1.55 (m), 1.50-1.40 (m), 1.35-1.27 (m), 1.25-1.12 (m), 1.05-0.92 (m), 0.90-0.82 (m).

f) Preparation of 4-ethyl-2-(2,2,6-trimethyl-1-cyclohexyl)-1,3-dioxolane

According to the above general procedure, using the corresponding diol, the title compound was obtained in 85% yield.

$^1$H NMR (360.1 MHz): 5.04 (s), 5.03 (s), 5.01 (broad s), 4.90 (s), 4.25-3.75 (m), 3.60-3.30 (m), 1.80-1.15 (m), 1.05-0.85 (m).

g) Preparation of 4,4,6-trimethyl-2-(2,2,6-trimethyl-1-cyclohexyl)-1,3-dioxane

According to the above general procedure, using the corresponding diol, the title compound was obtained in 82% yield.

$^1$H NMR (360.1 MHz): 4.96 (broad s, 1H, CH), 4.94 (broad s, 1H, CH), 3.85-3.71 (m, 1H+1H), 1.85-1.55 (m, 4H), 1.53-1.27 (m, 14H), 1.26 (broad s, 3H+3H), 1.20 (s, 3H), 1.19 (s, 3H), 1.16 (d, J=1.7 Hz, 3H), 1.14 (d, J=1.6, 3H), 1.04 (d, J=0.5, 3H), 1.02 (broad s, 3H), 1.0-0.86 (m, 2H), 0.85 (s, 3H), 0.82 (s, 3H).

Example 2

Preparation of a Perfuming Composition

A perfume, having an orange rosy connotation, was prepared by admixing the following ingredients:

| Ingredient | Parts by weight |
|---|---|
| Benzyl acetate | 100 |
| Carbinol acetate | 20 |
| Geranyle acetate | 20 |
| Phenylethyl acetate | 60 |
| 10%* (3Z)-hex-3-ene acetate | 30 |
| 1%* Phenylacetic acid | 30 |
| 10%* Aldehyde benzoic aldehyde | 40 |
| Aldehyde C 10 | 10 |
| Aldehyde C 9 | 10 |
| Aldehyde MNA | 5 |
| 10%* Phenylacetique aldehyde | 5 |
| 10%* Roman camomile essential oil | 20 |
| Citral | 10 |
| Cis-2-pentyl-1-cyclopentanol | 30 |
| 10%* Damascenone | 20 |
| Damascone Alpha | 5 |
| Diphenyloxyde | 40 |
| Citronellyl formiate | 10 |
| Geraniol | 100 |
| English glove essential oil | 10 |
| Hedione ®[1] | 50 |
| Ionone Beta | 60 |
| 10%* Methyl 2-nonynoate | 20 |
| Rose oxide | 5 |
| Phenethylol | 500 |
| Methyl phenylacetate | 20 |
| Phenylethyle phenylacetate | 60 |
| 10%* Phenylacetate | 10 |
| (3Z)-Hex-3-ene | 10 |
| Verdyl propionate | 100 |
| Prunella ®[2] | 20 |
| 2,2,2-Trichloro-1-phenylethyle acetate[3] | 200 |
| Amyle salicylate | 100 |
| 10%* 5-Methyl-3-heptanone-oxime | 40 |
| Styrax Essental oil | 30 |
| Wardia ®[2] - 184036 D | 100 |
| | 1900 |

*in dipropyleneglycol
[1] methyl dihydrojasmonate; origin: Firmenich SA, Switzerland
[2] compounded base; origin: Firmenich SA, Switzerland
[3] origin: Firmenich SA, Switzerland The addition of 300 parts by weight of 6-(dimethoxymethyl)-1,5,5-trimethyl-1-cyclohexene to the above-described perfuming composition transformed in a spectacular manner the initial white rose perfume into a rose-tea, this effect could have been obtained only using the compound 1,3-dibromo-2-methoxy-4-methyl-5-nitrobenzene which is no more available to the perfumer.

The addition of 100 parts by weight of 2-(2,2,c-3,t-6-tetramethyl-r-1-cyclohexyl)-1,3-dioxolane to the above-described perfuming composition transformed in a spectacular manner the initial white rose perfume by imparting a green-dew aspect as well as a woody, stem note.

The addition of 100 parts by weight of trans-2-(2,5,6,6-tetramethyl-2-cyclohexen-1-yl)-1,3-dioxolane boosted the ionones notes of the composition and imparted an orris character to the rose fragrance, while the addition of the same amount of a mixture of cis-2-(2,5,6,6-tetramethyl-2-cyclohexen-1-yl)-1,3-dioxolane and 2-(2,5,6,6-tetramethyl-1-cyclohexen-1-yl)-1,3-dioxolane converted said white rose into a red rose by imparting balsamic and Benjoin notes.

Example 3

Preparation of a Perfuming Composition

A perfume, for a detergent base, was prepared by admixing the following ingredients:

| Ingredient | Parts by weight |
| --- | --- |
| Verdyl acetate | 500 |
| 10-Undecen-1-al | 20 |
| Hexylcinnamic aldehyde | 1500 |
| Dihydromyrcenol | 400 |
| Ethyle-2-Methylbutytate | 20 |
| 70%* Galaxolide ®[1)] | 600 |
| Geraniol | 150 |
| Lemonile ®[2)] | 10 |
| Lilial ®[3)] | 400 |
| Linalol | 500 |
| Methylnaphtylcetone | 70 |
| Phenethylol | 100 |
| Orange essential oil | 150 |
| Sclareolate ®[4)] | 700 |
| Terpineol | 200 |
| Verdox ®[5)] | 150 |
| Vertofix ®[6)] Coeur | 220 |
| 2,4-Dimethyl-3-cyclohexene-1-carbaldehyde | 10 |
|  | 5700 |

*in myristate d'isopropyle
[1)] 1,3,4,6,7,8-hexahydro-4,6,6,7,8,8-hexamethyl-cyclopenta-g-2-benzopyrane; origin: International Flavors & Fragrances, USA
[2)] 3,7-dimethyl-2/3,6-nonadienenitrile; origin: Givaudan-Roure SA, Vernier, Switzerland
[3)] 3-(4-tert-butylphenyl)-2-methylpropanal; origin: Givaudan-Roure SA, Vernier, Switzerland
[4)] propyl (S)-2-(1,1-dimethylpropoxy)propanoate; origin: Firmenich SA, Switzerland
[5)] 2-tert-butyl-1-cyclohexyl acetate; origin: International Flavors & Fragrances, USA
[6)] methyl cedryl ketone; origin: International Flavors & Fragrances, USA The addition of 100 parts by weight of 6-(dimethoxymethyl)-1,5,5-trimethyl-1-cyclohexene to the above-described perfuming composition imparted a damascony, spicy aspect, while reinforcing the woody note provided by the Vertofix®.

The addition of 300 parts by weight of 2-(2,2,c-3,t-6-tetramethyl-r-1-cyclohexyl)-1,3-dioxolane to the above-described perfuming composition became more woody, less floral et reinforced the cologne aspect.

The addition of 300 parts by weight of trans-2-(2,5,6,6-tetramethyl-2-cyclohexen-1-yl)-1,3-dioxolane boosted the ionones notes of the composition and imparted an orris character with an ambery bottom note, while the addition of the same amount of a mixture of cis-2-(2,5,6,6-tetramethyl-2-cyclohexen-1-yl)-1,3-dioxolane and 2-(2,5,6,6-tetramethyl-1-cyclohexen-1-yl)-1,3-dioxolane imparted a clear ambery-woody character, with an orris note.

What is claimed is:

1. A compound of formula (I):

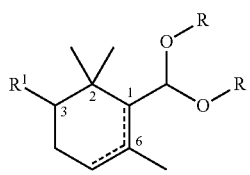

(I)

wherein one dotted line indicates the presence of a carbon-carbon single or double bond and the other dotted line indicates the presence of a carbon-carbon single bond;
$R^1$ represents a methyl or ethyl group; and
each R, taken alone, simultaneously or independently, represents a $C_{1-3}$ alkyl or alkenyl group; or the R groups, taken together, represent a $C_{2-6}$ hydrocarbon group optionally comprising an oxygen atom;
in the form of any one of its stereoisomers or in the form of a mixture thereof.

2. The compound according to claim 1, in the form of a mixture of stereoisomers comprising more than 50% (w/w) of the stereoisomer, wherein the substituents at positions 1 and 6 of the cyclohexane ring are in a cis relative configuration, and when $R^1$ is a methyl group the substituents at positions 3 and 6 of the cyclohexane ring are in a trans relative configuration.

3. The compound according to claim 1, specifically as trans-2-(2,5,6,6-tetramethyl-2-cyclohexen-1-yl)-1,3-dioxolane, 2-[(1RS,3RS,6RS)-2,2,3,6-tetramethylcyclohexyl]-1,3-dioxolane, 2-[(1RS,3RS,6SR)-2,2,3,6-tetramethylcyclohexyl]-1,3-dioxolane or 2-(2,2,c-3,t-6-Tetramethyl-r-1-cyclohexyl)-1,3-dioxolane.

4. A perfuming composition comprising
i) at least one compound as defined in claim 1;
ii) at least one ingredient selected from the group consisting of a perfumery carrier and a perfumery base; and
iii) optionally at least one perfumery adjuvant.

5. A perfumed article comprising:
i) at least one compound of formula (I), as defined in claim 1; and
ii) a fine or functional perfumery base.

6. The perfumed article according to claim 5, wherein the fine or functional perfumery base is a perfume, a fabric care product, a body-care product, an air care product or a home care product.

7. The perfumed article according to claim 5, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

8. A method to confer, enhance, improve or modify the odor properties of a perfuming composition or of a perfumed article, which method comprises adding to the composition or article an effective amount of at least a compound of formula (I):

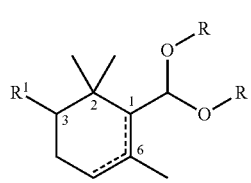

(I)

wherein one dotted line indicates the presence of a carbon-carbon single or double bond and the other dotted line indicates the presence of a carbon-carbon single bond;
$R^1$ represents a hydrogen atom or a methyl or ethyl group; and
each R, taken alone, simultaneously or independently, represents a $C_{1-3}$ alkyl or alkenyl group; or the R groups, taken together, represent a $C_{2-6}$ hydrocarbon group optionally including an oxygen atom;

in the form of any one of its stereoisomers or in the form of a mixture thereof.

9. The method according to claim 8, wherein the compound (I) is of formula (II):

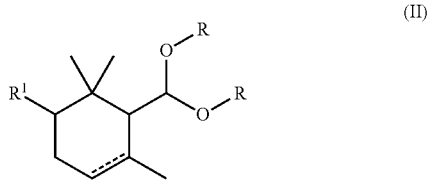

wherein the dotted line indicates the presence of a carbon-carbon single or double bond;

$R^1$ represents a hydrogen atom or a methyl group; and each R, taken alone, simultaneously or independently, represents a $C_{1-2}$ alkyl group; or the R groups, taken together, represent a $C_{2-5}$ hydrocarbon group.

10. The method according to claim 9, wherein in the compound (II) the dotted line indicates the presence of a carbon-carbon single bond; and the compound (II) is in the form of a mixture of stereoisomers comprising more than 50% (w/w) of the stereoisomer wherein the substituents at position 1 and 6 of the cyclohexane ring are in a trans relative configuration, and when $R^1$ is a methyl group the substituents at position 3 and 6 of the cyclohexane ring are in a trans relative configuration.

11. The method according to claim 8, wherein the compound of formula (I) is trans-2-(2,5,6,6-tetramethyl-2-cyclohexen-1-yl)-1,3-dioxolane, 2-[(1RS,3RS,6RS)-2,2,3,6-tetramethylcyclohexyl]-1,3-dioxolane, 2-[(1RS,3RS,6SR)-2,2,3,6-tetramethylcyclohexyl]-1,3-dioxolane or 2-(2,2,c-3,t-6-Tetramethyl-r-1-cyclohexyl)-1,3-dioxolane.

12. The method according to claim 8, wherein the composition is a perfuming composition comprising:
i) at least one compound as defined in claim 8;
ii) at least one ingredient selected from the group consisting of a perfumery carrier and a perfumery base; and
iii) optionally at least one perfumery adjuvant.

13. The method according to claim 8, wherein the perfumed article comprises:
i) at least one compound of formula (I), as defined in claim 8; and
ii) a fine or functional perfumery base.

14. The method according to claim 13, wherein the fine or functional perfumery base is a perfume, a fabric care product, a body-care product, an air care product or a home care product.

15. The method according to claim 13, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

\* \* \* \* \*